United States Patent [19]
Love

[11] Patent Number: 5,573,914
[45] Date of Patent: Nov. 12, 1996

[54] DNA/RNA TARGET AND SIGNAL AMPLIFICATION

[75] Inventor: Jack D. Love, Rockville, Md.

[73] Assignee: Gen Trak, Inc, Plymouth Meeting, Pa.

[21] Appl. No.: 441,678

[22] Filed: May 15, 1995

Related U.S. Application Data

[63] Continuation of Ser. No. 226,940, Apr. 13, 1994, abandoned, which is a continuation of Ser. No. 756,600, Sep. 10, 1991, abandoned.

[51] Int. Cl.$^6$ .............................. C12Q 1/68; C12P 19/34
[52] U.S. Cl. ................................................ 435/6; 435/91.2
[58] Field of Search .................................. 435/5, 6, 91.2, 435/91.21; 935/77, 78

[56] References Cited

U.S. PATENT DOCUMENTS

| | | | |
|---|---|---|---|
| 4,581,333 | 4/1986 | Kourilsky et al. | 435/6 |
| 4,683,195 | 7/1987 | Mullis et al. | 435/6 |
| 4,683,202 | 7/1987 | Mullis | 435/91.1 |
| 4,749,647 | 6/1988 | Thomas et al. | 435/6 |
| 4,786,600 | 11/1988 | Kramer et al. | 435/6 |
| 4,851,331 | 7/1989 | Vary et al. | 435/6 |
| 4,882,269 | 11/1989 | Schneider et al. | 435/6 |
| 4,957,858 | 9/1990 | Chu et al. | 435/6 |
| 4,965,188 | 10/1990 | Mullis et al. | 435/6 |
| 4,994,373 | 2/1991 | Stavrianopoulos et al. | 435/6 |
| 5,112,734 | 5/1992 | Kramer et al. | 435/6 |
| 5,118,605 | 6/1992 | Urdea | 435/6 |

FOREIGN PATENT DOCUMENTS

| | | |
|---|---|---|
| 0369775 | 11/1989 | European Pat. Off. . |
| 20408295 | 1/1991 | European Pat. Off. . |
| 0450594A2 | 4/1991 | European Pat. Off. . |
| 2131599 | 5/1990 | Japan . |
| WO87/03622 | 6/1987 | WIPO . |
| WOA89/01050 | 2/1989 | WIPO . |
| WO89/06700 | 7/1989 | WIPO . |
| WO91/10746 | 7/1991 | WIPO . |
| WO91/17442 | 11/1991 | WIPO . |
| WO92/12261 | 7/1992 | WIPO . |
| WO92/14843 | 9/1992 | WIPO . |

OTHER PUBLICATIONS

Chu, B. C. F., et al., "Synthesis of an Amplifiable Reporter RNA for Bioassays", *Nucleic Acids Research*, vol. 14, No. 14, pp. 5591–5603 (1986).

Diamandis, E. P., "Detection Techniques for Immunoassay and DNA Probing Applications", *Clinical Biochemistry*, vol. 23, pp. 437–443, especially pp. 441–442 (Oct., 1990).

Kwoh, D. Y., et al., "Target Amplification Systems in Nucleic Acid–Based Diagnostic Approaches", *American Biotechnology Laboratory*, vol. 8, No. 13, pp. 14–25, especially pp. 20, 24, 25 (1990).

Thompson, J. D., et al., "Current Concepts in Quantitative Hybridization", *Clinical Biochemistry*, vol. 23, pp. 261–266, especially p. 265 (Aug. 1990).

Guatelli et al., "Isothermal, in vitro amplification of nucleic acids by a multienzyme reaction modeled after retroviral replication," *Proc. Natl. Acad. Sci. USA* 87:1874–1878 (1990).

Kwoh et al., "Transcription–based amplification system and detection of amplified human immunodeficiency virus type 1 with a bead–based sandwich hybridization format," *Proc. Natl. Acad Sci. USA* 86:1173–1177 (1989).

Fahy et al., Self–sustained sequence replication (3SR): an isothermal transcription–based amplification system alternative to PCR, *PCR Methods Appl.* 1:25–33 (1991).

Resto et al., Amplification of protein expression in a cell free system, *Nucl. Acids Res.* 20:5979–5983 (1992).

Kramer et al. Am. Biol. Clin 48/6:409–411 (1990) "Amplifiable hybridization probes".

D. Y. Kwoh et al. Proc. Natl. Acad. Sci. USA 86, 1173–1177 (1989).

Primary Examiner—W. Gary Jones
Assistant Examiner—Eggerton Campbell
Attorney, Agent, or Firm—Jones & Askew

[57] ABSTRACT

A process for detecting the presence or absence of a specific nucleic acid sequence or antibody in a sample using an oligonucleotide to bind to the nucleic acid sequence or antibody to be detected, forming double-stranded nucleic acid sequence using the bound oligonucleotide in conjunction with another oligonucleotide or DNA synthesis, synthesizing RNA transcripts from the thus-formed double-stranded nucleic acid sequence, and detecting the existence of the RNA transcripts, and oligonucleotides and kits useful in carrying out such a process.

13 Claims, 6 Drawing Sheets

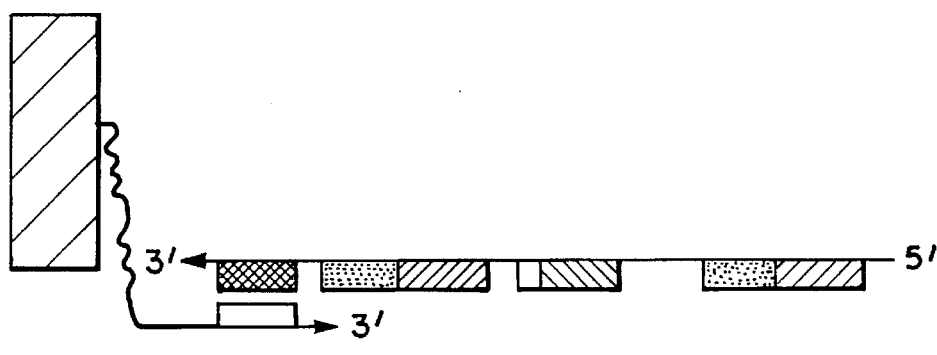
Cut with Restriction Enzyme
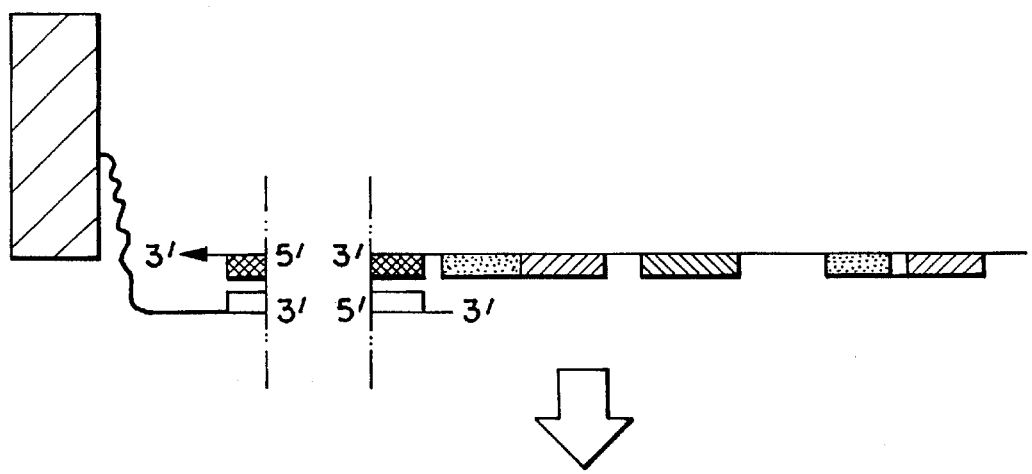
Filter to Collect Specifically Bound Probe
All other Steps the same as Methods 1, 2, or 3
Fig. 4

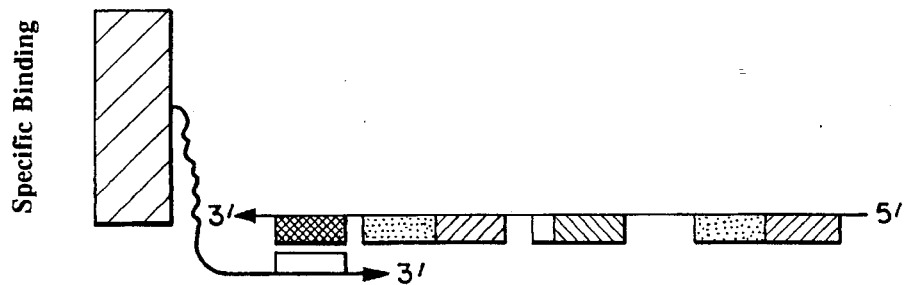
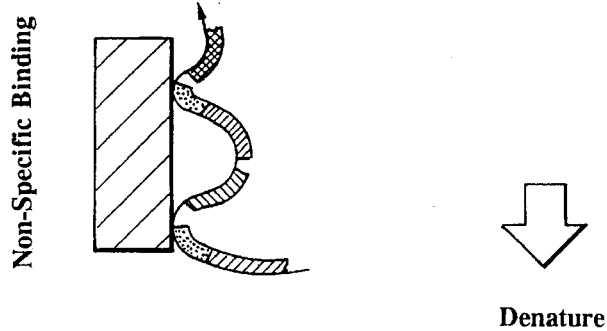
Denature
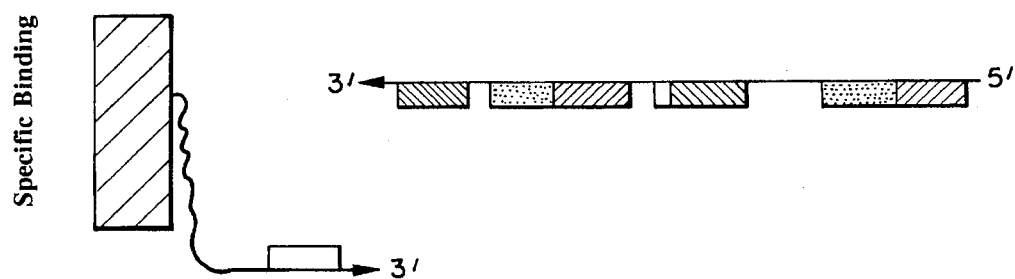
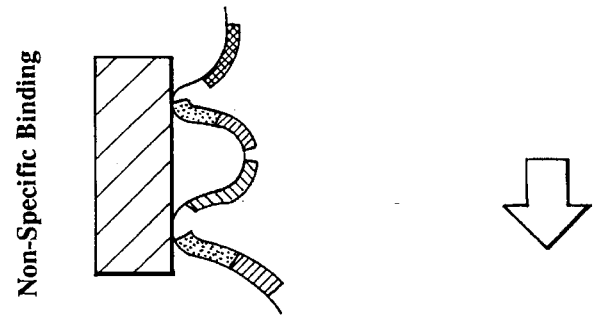
Filter to Collect Specifically Bound Probe
All other Steps the same as
Methods 1 or 2
Fig_5

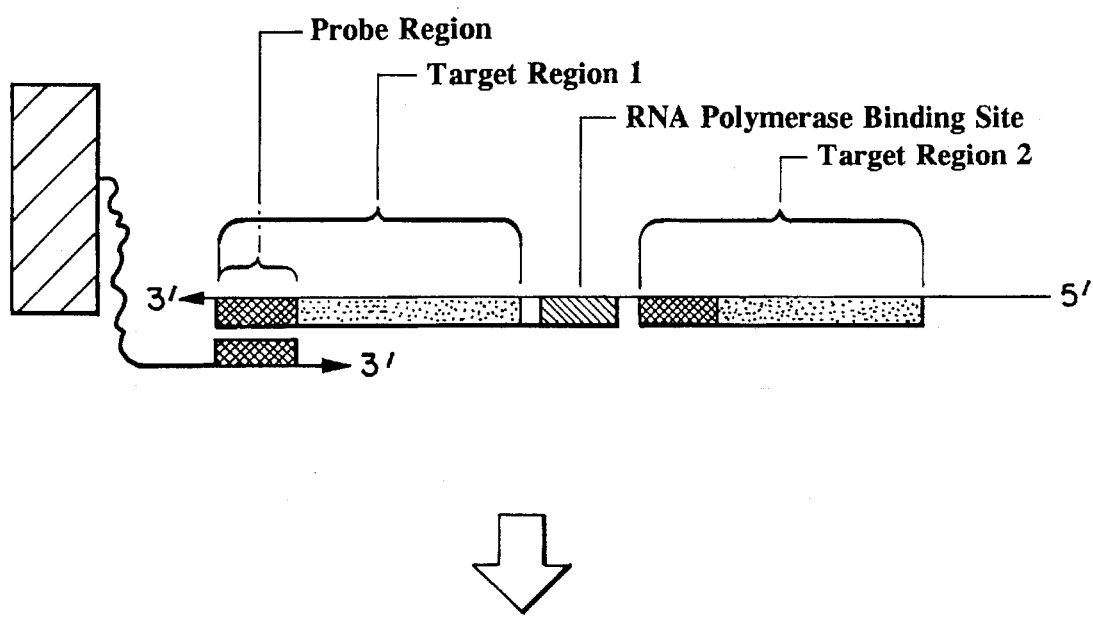
All other Steps the same as Methods 1, 2, or 3
Fig_6

DNA/RNA TARGET AND SIGNAL AMPLIFICATION

This is a continuation application under 37 CFR 1.62 of prior application Ser. No. 08/226,940 filed on Apr. 13, 1994, abandoned which is a continuation of application Ser. No. 07/756,600, filed Sep. 10, 1991 abandoned.

TECHNICAL FIELD

The present invention relates to processes for detecting the presence or absence of nucleic acid sequences and antibodies in samples and oligonucleotides and kits useful in carrying out such processes.

BACKGROUND OF THE INVENTION

The present invention involves processes to detect nucleic acid sequences and antibodies in samples by amplifying signals associated with the existence of such nucleic acid sequences and antibodies. In particular, an oligonucleotide sequence is bound to the nucleic acid sequence to be detected or, through a connector molecule, to an antibody to be detected, and that oligonucleotide is used to form a double-stranded nucleic acid sequence which is used to synthesize relatively large quantities of RNA transcripts in a short period of time for detection.

Many target and signal amplification techniques have been described in the literature, but none of these techniques is believed to offer the combination of specificity, simplicity, and speed of the present invention. Some of these various techniques are described below.

a) Polymerase Chain Reaction (PCR) PCR is described in Saiki et al. (1985), *Science*, 230 1350. PCR consists of repeated cycles of DNA polymerase generated primer extension reactions. The target DNA is heat denatured and two oligonucleotides, which bracket the target sequence on opposite strands of the DNA to be amplified, are hybridized. These oligonucleotides become primers for use with DNA polymerase. The DNA is copied by primer extension to make a second copy of both strands. By repeating the cycle of heat denaturation, primer hybridization and extension, the target DNA can be amplified a million fold or more in about two to four hours. PCR is a molecular biology tool which must be used in conjunction with a detection technique to determine the results of amplification. The advantage of PCR is that it may increase sensitivity by amplifying the amount of target DNA by 1 million to 1 billion fold in about 4 hours. The disadvantage is that contamination may result in false positive results (i.e., reduced specificity).

b) Transcription Amplification (TAS) TAS utilizes RNA transcription to amplify a DNA or RNA target and is described in Kwoh et al. (1989) *Proc. Natl. Acad. Sci. USA* 86, 1173. TAS uses two phases of amplification. In phase 1 of TAS a duplex cDNA is formed containing an overhanging, single stranded T7 transcription promoter by hybridizing a polynucleotide to the target. The DNA is copied by reverse transcriptase into a duplex form. This is heat denatured and a primer for the opposite strand from that with the T7 region is hybridized. Using this primer, reverse transcriptase is again added to create a double stranded cDNA, which now has a double stranded (active) T7 polymerase binding site. T7 RNA polymerase transcribes the duplex to create a large quantity of single stranded RNA. This is the completion of phase one of TAS. In phase 2, the primer is again used. This time it is hybridized to the new RNA and again converted to duplex cDNA. The duplex is heat denatured and the cycle is continued as before. In contrast to PCR where two copies of the target are generated each cycle, the advantage of TAS is that between 10 and 100 copies of each target molecule are produced with each cycle. This means that $10^6$ fold amplification can be achieved in only 4 to 6 cycles, but this still takes 3–4 hours. The major disadvantage of TAS is the number of enzyme addition steps and the heat denaturation requirements.

c) Transcriptions Amplification (3SR) In a modification of TAS, known as 3SR, enzymatic degradation of the RNA of the RNA/DNA heteroduplex is used instead of heat denaturation, as described in Guatelli et al. (1990) *Proc. Natl. Acad. Sci.* USA 87, 1874. RNAse H and all other enzymes are added to the reaction and all steps occur at the same temperature and without further reagent additions. Following this process, amplification of $10^6$ to $10^9$ have been achieved in 1 hour at 42° C.

d) Ligation Amplification (LAR/LAS) Ligation amplification reaction or ligation amplification system uses DNA ligase and four oligonucleotides, two per target strand. This technique is described in Wu, D. Y. and Wallace, R. B. (1989) *Genomics* 4, 560. The oligonucleotides hybridize to adjacent sequences on the target DNA and are joined by the ligase. The reaction is heat denatured and the cycle repeated. LAR suffers from the fact that the ligases can join the oligonucleotides even when they are not hybridized to the target DNA. This results in a high background. In addition, LAR is not an efficient reaction and therefore currently requires about five hours for each cycle. Thus, the amplification takes a couple of days.

e) Q Beta RNA Replication In this technique, RNA replicase for the bacteriophage Q Beta, which replicates single stranded RNA, is used to amplify the target DNA, as described in Lizardi et al. (1988) *Bio/Technology* 6, 1197. First, the target DNA is hybridized to a primer containing T7 promoter and a Q Beta 5' sequence region. Using this primer, reverse transcriptase generates a cDNA connecting the primer to its 5' end in the process. These two steps are similar to the TAS protocol. The resulting heteroduplex is heat denatured. Next, a second primer containing a Q Beta 3' sequence region is used to initiate a second round of cDNA synthesis. This results in a double stranded DNA containing both 5' and 3' ends of the Q-Beta bacteriophage as well as an active T7 RNA polymerase binding site. T7 RNA polymerase then transcribes the ds-DNA into new RNA, which mimics the Q Beta virus. After extensive washing to remove any unhybridized probe, the new RNA is eluted from the target and replicated by Q Beta replicase. The latter reaction created $10^7$ amplification in 20 minutes. Significant background may be formed due to minute amounts of probe RNA that is non-specifically retained during the reaction.

f) Chiron Signal Amplification The Chiron system, as described in Urdea et al. (1987) Gene 61, 253, is extremely complex. It utilizes 12 capture oligonucleotide probes, 36 labeled oligonucleotides, 20 biotinylated immobilization probes that are cross-linked to 20 more enzyme labeled probes. This massive conglomerate is built-up in a stepwise fashion requiring numerous washing and reagent addition steps. Amplification is limited because there is no cycle. The probes simply form a large network.

g) ImClone Signal Amplification ImClone utilizes a network concept similar to Chiron, but the approach is completely different. The ImClone technique is described in Kohlbert et al. (1989) *Mol and Cell Probes* 3, 59. ImClone first binds a single stranded M13 phage DNA containing targeted probe. To this bound circular DNA is then hybridized about five additional DNA fragments that only bind to one end and the other end hangs freely out in the solution. Another probe set is then hybridized to the hanging portion of the previous set of probes. The latter set is either labeled directly with an enzyme or it is biotinylated. If it is biotinylated, then detection is via a streptavidin enzyme complex. In either case, detection is through an enzyme color reaction. Like the Chiron method, ImClone relies on build-up of a large network. Because there is no repeated cycle, the reaction is not geometrically expanded, resulting in limited amplification.

BRIEF SUMMARY OF THE INVENTION

The present invention pertains to a process for detecting the presence or absence of at least one specific nucleic acid sequence in a sample containing a nucleic acid or mixture of nucleic acids, which process comprises immobilizing the specific nucleic acid sequence to be detected, treating the sample with a first oligonucleotide sequence under hybridizing conditions such that a portion of the first oligonucleotide sequence hybridizes to the specific nucleic acid sequence to be detected and a portion of the first oligonucleotide sequence does not hybridize to the specific nucleic acid sequence to be detected, wherein the portion of the first oligonucleotide sequence which does not hybridize to the specific nucleic acid sequence to be detected forms a RNA polymerase binding site and a nucleotide sequence capable of transcribing RNA only when hybridized to a complementary nucleotide sequence, treating the sample to remove any of first oligonucleotide sequence which is not hybridized to the specific nucleic acid sequence to be detected, treating the sample with a second oligonucleotide sequence under hybridizing conditions such that the second oligonucleotide sequence hybridizes to the portion of the first oligonucleotide sequence which does not hybridize to the specific nucleic acid sequence to be detected and forms an active RNA polymerase binding site and nucleotide sequence capable of transcribing RNA, treating the sample with RNA polymerase and nucleotide triphosphates such that the nucleotide sequence formed between a portion of the first oligonucleotide sequence and a portion of the second oligonucleotide sequence results in the synthesis of RNA transcripts, and determining whether the RNA transcripts were synthesized.

Alternatively, the sample may be treated, after immobilization of the specific nucleic acid sequence to be detected, with an oligonucleotide sequence under hybridizing conditions such that a portion of the oligonucleotide sequence hybridizes to the 3' end of the specific nucleic acid sequence to be detected which acts as a primer for the oligonucleotide sequence and a portion of the oligonucleotide sequence does not hybridize to the specific nucleic acid sequence to be detected, wherein the portion of the oligonucleotide sequence which does not hybridize to the specific nucleic acid sequence to be detected forms a RNA polymerase binding site and a nucleotide sequence capable of transcribing RNA only when an extension product is synthesized from the primer which is complementary to the oligonucleotide sequence, treating the sample with DNA polymerase, RNA polymerase, and nucleotide triphosphates such that an extension product is synthesized from the primer which is complementary to the oligonucleotide sequence to form an active RNA polymerase binding site and nucleotide sequence capable of transcribing RNA which results in the synthesis of RNA transcripts, and determining whether the RNA transcripts were synthesized.

The present invention is also applicable to the detection of the presence or absence of antibodies through use of a "connector molecule."

It is an object of the present invention to provide a process for the detection of nucleic acid sequences and antibodies in samples with a high degree of specificity and simplicity in a short period of time.

It is another object of the present invention to provide a process for the detection of nucleic acid sequences and antibodies wherein oligonucleotide sequences act as primers, resulting in the repetitive synthesis of additional transcripts.

It is a further object of the present invention to provide oligonucleotide sequences for use in efficiently and precisely detecting the presence or absence of nucleic acid sequences and antibodies in samples.

It is yet another object of the present invention to provide kits useful in quickly carrying out processes for the detection of the presence or absence of nucleic acid sequences and antibodies in samples.

These and other objects and advantages of the present invention will be apparent from the description of the invention provided herein.

BRIEF DESCRIPTION OF THE DRAWINGS

FIG. 4 depicts a process for reducing background by the use of restriction enzyme digestion.

FIG. 5 depicts another process for reducing background by denaturation of the specifically bound probe.

FIG. 6 depicts another process for detecting target nucleic acid sequences in a sample.

DESCRIPTION OF THE PREFERRED EMBODIMENTS

Figure 1:
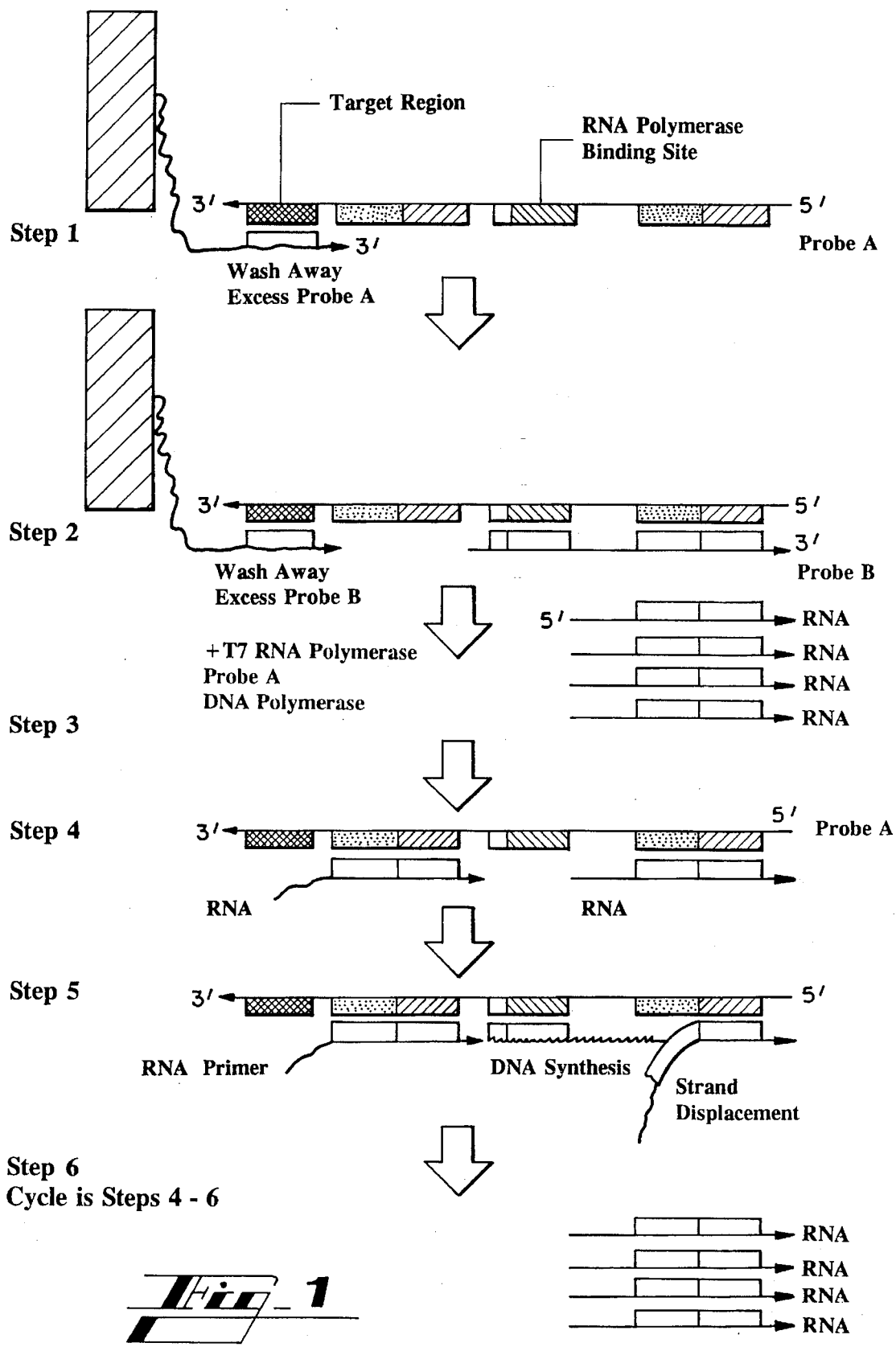
FIG. 1 depicts a preferred process of the present invention for detecting nucleic acid sequences in a sample utilizing two oligonucleotides.
Figure 2:
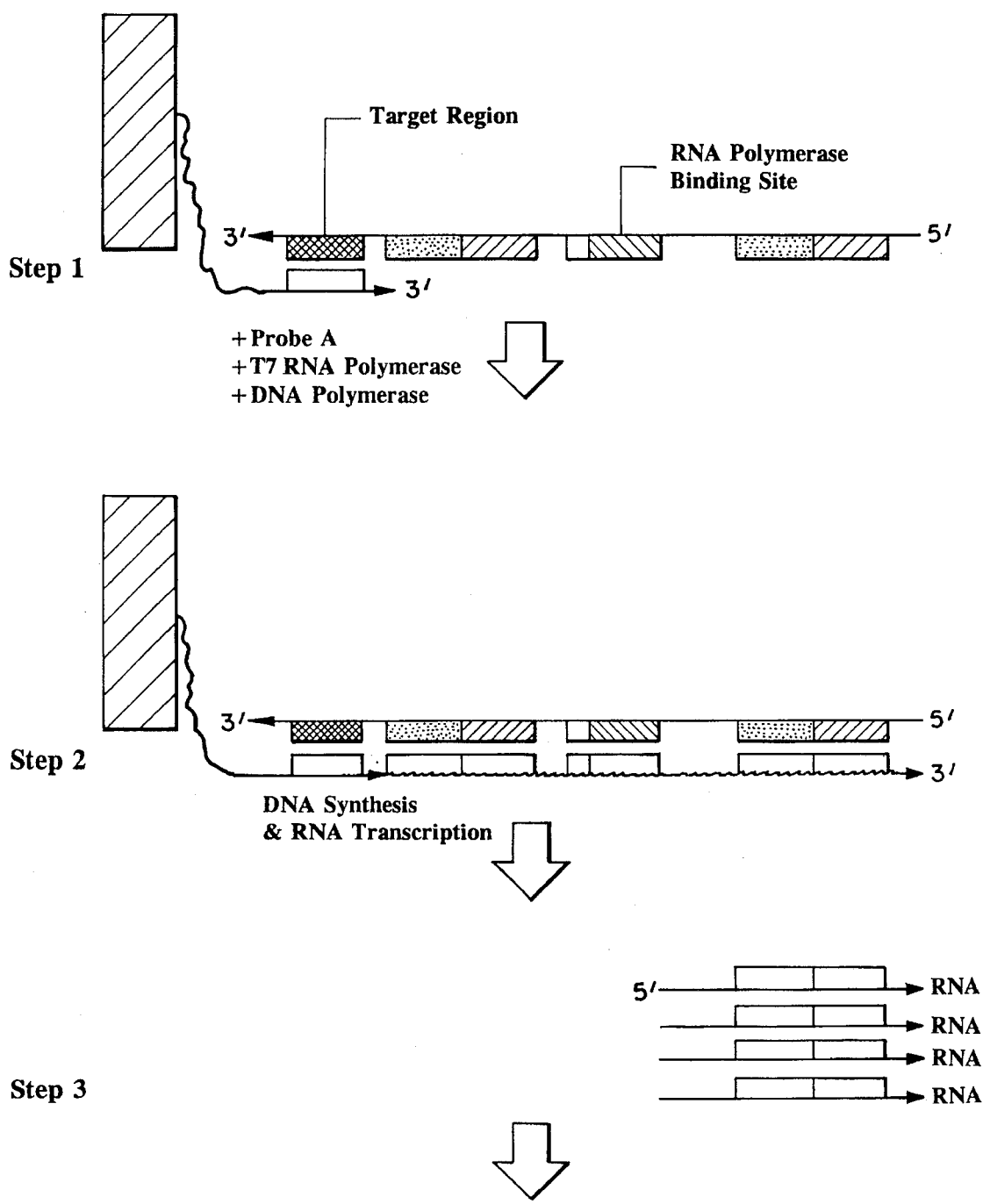
FIG. 2 depicts another preferred process of the present invention for detecting nucleic acid sequences in a sample utilizing one oligonucleotide and DNA synthesis.

The present invention is predicated on binding an oligonucleotide to the specific nucleic acid sequence or antibody desired to be detected in a sample, and then using that oligonucleotide to form a double-stranded nucleic acid sequence, by using either another oligonucleotide or DNA synthesis, and thereby synthesizing readily detectable quantities of RNA transcripts.

The oligonucleotide sequence to be used in conjunction with the present invention comprises a portion which binds to a specific substance to be detected in a sample and a portion which does not bind to said specific substance to be detected, wherein said portion of said oligonucleotide sequence which does not bind to said specific substance to be detected forms a RNA polymerase binding site and a nucleotide sequence capable of transcribing RNA when hybridized to a complementary nucleotide sequence.

In particular, the present invention involves a process for detecting the presence or absence of at least one specific nucleic acid sequence in a sample containing a nucleic acid or mixture of nucleic acids, which process comprises:

(a) immobilizing the specific nucleic acid sequence to be detected, (b) treating the sample with a first oligonucleotide sequence under hybridizing conditions such that a portion of the first oligonucleotide sequence hybridizes to the specific nucleic acid sequence to be detected and a portion of the first oligonucleotide sequence does not hybridize to the specific nucleic acid sequence to be detected, wherein the portion of the first oligonucleotide sequence which does not hybridize to the specific nucleic acid sequence to be detected forms a RNA polymerase binding site and a nucleotide sequence capable of transcribing RNA when hybridized to a complementary nucleotide sequence, (c) treating the sample to remove any of first oligonucleotide sequence which is not hybridized to the specific nucleic acid sequence to be detected, (d) treating the sample with a second oligonucleotide sequence under hybridizing conditions such that the second oligonucleotide sequence hybridizes to the portion of the first oligonucleotide sequence which does not hybridize to the specific acid sequence to be detected and forms a RNA polymerase binding site and nucleotide sequence capable of transcribing RNA, (e) treating the sample with RNA polymerase and nucleotide triphosphates such that the nucleotide sequence formed between a portion of the first oligonucleotide sequence and a portion of the second oligonucleotide sequence results in the synthesis of RNA transcripts, and (f) determining whether the RNA transcripts were synthesized.

This process is preferably modified such that the sample at step (e) is further treated with the first oligonucleotide sequence capable of hybridizing to the RNA transcripts and with DNA polymerase such that the first oligonucleotide sequence hybridizes to the RNA transcripts which act as primers for synthesis of an extension nucleotide sequence complementary to the first oligonucleotide sequence to form a RNA polymerase binding site and a nucleotide sequence capable of transcribing RNA which results in the synthesis of additional RNA transcripts. More preferably, the step of treating the sample with the first oligonucleotide sequence and with DNA polymerase is repeated. The RNA transcripts may also be virus fragments that are replicated through use of a RNA virus replicase.

Another preferred modification is to hybridize the first oligonucleotide sequence to the specific nucleic acid sequence to be detected at the 3' end of the first oligonucleotide sequence and then in treating the sample in step (c) to remove any of first oligonucleotide sequence which is not hybridized to the specific nucleic acid sequence to be detected including the treatment of the sample with a single strand specific 3'–5' exonuclease such that the portion of the first oligonucleotide sequence which forms a RNA polymerase binding site when hybridized to a complementary nucleotide sequence is cleaved from any of first oligonucleotide sequence which is not hybridized to the specific nucleic acid sequence to be detected.

As an alternative, or in addition to these other modifications, the sample at step (c) may be further treated to separate the first oligonucleotide sequence from the specific nucleic acid sequence to be detected and the sample treated to remove any insoluble components. The sample would, therefore, include primarily the (soluble) oligonucleotide sequence which had been bound to the specific nucleic acid sequence to be detected in the sample, thereby further decreasing any background. The first oligonucleotide sequence may be separated from the specific nucleic acid sequence to be detected by any suitable means, such as by denaturation.

Similarly, the sample at step (d) may be further treated to separate the first oligonucleotide sequence from the specific nucleic acid sequence to be detected resulting in a soluble portion of the first oligonucleotide sequence hybridized to the second oligonucleotide sequence forming a RNA polymerase binding site and nucleotide sequence capable of transcribing RNA, with the sample thereafter being treated to remove any insoluble components. The first oligonucleotide sequence can be separated from the specific nucleic acid sequence to be detected by any suitable means, e.g., through use of a restriction enzyme which cleaves the portion of the first oligonucleotide sequence hybridized to the specific nucleic acid sequence to be detected. Again, the sample would thereby include primarily the (soluble) oligonucleotide sequence which had been bound to the specific nucleic acid sequence to be detected in the sample, thereby further decreasing any background.

The present inventive process may also be useful in amplifying the targeted nucleic acid sequence, or a portion thereof, in the sample by selecting the first oligonucleotide sequence such that the portion of the first oligonucleotide sequence which hybridizes to the second oligonucleotide sequence includes a nucleotide sequence identical to the portion of the first oligonucleotide sequence which hybridizes to the specific nucleic acid sequence to be detected. In such an event, the portion of the first oligonucleotide sequence which hybridizes to the second oligonucleotide sequence is preferably identical to the portion of the first oligonucleotide sequence which hybridizes to the specific nucleic acid sequence to be detected.

An alternative to using a second oligonucleotide to hybridize to the first oligonucleotide to form a double-stranded nucleic acid sequence capable of synthesizing RNA transcripts is to use the target sequence of the specific nucleic acid sequence to be detected in a sample as a primer, in conjunction with DNA synthesis, to prepare the complementary nucleotides to yield the double-stranded nucleic acid sequence capable of synthesizing RNA transcripts. Such a process for detecting the presence or absence of at least one specific nucleic acid sequence in a sample containing a nucleic acid or mixture of nucleic acids comprises:

(a) immobilizing the specific nucleic acid sequence to be detected, (b) treating the sample with an oligonucleotide sequence under hybridizing conditions such that a portion of the oligonucleotide sequence hybridizes to the 3' end of the specific nucleic acid sequence to be detected which acts as a primer for the oligonucleotide sequence and a portion of the oligonucleotide sequence does not hybridize to the specific nucleic acid sequence to be detected, wherein the portion of the oligonucleotide sequence which does not hybridize to the specific nucleic acid sequence to be detected forms a RNA polymerase binding site and a nucleotide sequence capable of transcribing RNA when an extension product is synthesized from the primer which is complementary to the oligonucleotide sequence, (c) treating the sample with DNA polymerase, RNA polymerase, and nucleotide triphosphates such that an extension product is synthesized from the primer which is complementary to the oligonucleotide sequence to form a RNA polymerase binding site and nucleotide sequence capable of transcribing RNA which results in the synthesis of RNA transcripts, and (d) determining whether the RNA transcripts were synthesized.

In a fashion similar to the present inventive process involving the second oligonucleotide, the sample at step (c) can be further treated with the oligonucleotide sequence capable of hybridizing to the RNA transcripts and with DNA polymerase such that the oligonucleotide sequence hybridizes to the RNA transcripts which act as primers for synthesis of an extension nucleotide sequence complementary to the oligonucleotide sequence to form a RNA polymerase binding site and a nucleotide sequence capable of transcribing RNA which results in the synthesis of additional RNA transcripts. Also, the step of treating the sample with the oligonucleotide sequence and with DNA polymerase may be repeated, and the RNA transcripts may be virus fragments which are replicated through use of a RNA virus replicase.

The present inventive process also has applicability to the detection of antibodies in samples. Specifically, the present inventive process for detecting the presence or absence of at least one specific antibody in a sample containing an antibody or mixture of antibodies comprises:

(a) immobilizing either the specific antibody to be detected in the sample or an antigen which binds to the specific antibody to be detected, (b) contacting the sample with an antigen which binds to the antibody to form an antibody-antigen complex which is immobilized, (c) treating the sample to remove any of the antibody or the antigen which are not bound, (d) treating the sample with a first oligonucleotide sequence such that a portion of the first oligonucleotide sequence binds to the antibody-antigen complex and a portion of the first oligonucleotide sequence does not bind to the antibody-antigen complex, wherein the portion of the first oligonucleotide sequence which does not bind to the antibody-antigen complex forms a RNA polymerase binding site and a nucleotide sequence capable of transcribing RNA when hybridized to a complementary nucleotide sequence, (e) treating the sample to remove any of first oligonucleotide sequence which is not bound to the antibody-antigen complex, (f) treating the sample with a second oligonucleotide sequence under hybridizing conditions such that the second oligonucleotide sequence hybridizes to the portion of the first oligonucleotide sequence which does not bind to the antibody-antigen complex and forms a RNA polymerase binding site and nucleotide sequence capable of transcribing RNA, (g) treating the sample with RNA polymerase and nucleotide triphosphates such that the nucleotide sequence formed between a portion of the first oligonucleotide sequence and a portion of the second oligonucleotide sequence results in the synthesis of RNA transcripts, and (h) determining whether the RNA transcripts were synthesized.

As with the detection of nucleic acid sequences, the sample, specifically at step (g), can be further treated with the first oligonucleotide sequence capable of hybridizing to the RNA transcripts and with DNA polymerase such that the first oligonucleotide sequence hybridizes to the RNA transcripts which act as primers for synthesis of an extension nucleotide sequence complementary to the first oligonucleotide sequence to form a RNA polymerase binding site and a nucleotide sequence capable of transcribing RNA which results in the synthesis of additional RNA transcripts. The step of treating the sample with the first oligonucleotide sequence and with DNA polymerase may, of course, be repeated, and the RNA transcripts may be virus fragments which are replicated through use of a RNA virus replicase.

While the first oligonucleotide may bind to the antibody in any suitable manner, preferably the first oligonucleotide sequence is biotinylated and binds to the antibody-antigen complex through a streptavidin-complexed molecule.

In addition, the second oligonucleotide sequence may act as a primer for the first oligonucleotide sequence and the RNA polymerase binding site and nucleotide sequence capable of transcribing RNA are formed by the addition of DNA polymerase to the sample such that an extension product is synthesized from the primer which is complementary to the first oligonucleotide sequence.

As is apparent from the discussion of the present invention in terms of the process of detecting nucleic acid sequences and antibodies in samples, the present invention involves the use of an oligonucleotide sequence comprising a portion which binds to a specific substance to be detected in a sample and a portion which does not bind to the specific substance to be detected, wherein the portion of the oligonucleotide sequence which does not bind to the specific substance to be detected forms a RNA polymerase binding site and a nucleotide sequence capable of transcribing RNA when hybridized to a complementary nucleotide sequence or when synthesized from a primer.

Kits for use in conjunction with the present invention in detecting the presence or absence of at least one specific substance in a sample can be devised which utilize such a first oligonucleotide sequence, along with a second oligonucleotide sequence which hybridizes with the portion of the first oligonucleotide sequence which does not hybridize to the specific acid sequence to be detected and forms a RNA polymerase binding site and nucleotide sequence capable of transcribing RNA, RNA polymerase, nucleotide triphosphates, and a means for determining the presence of RNA transcripts synthesized from the nucleotide sequence capable of transcribing RNA. Alternatively such a kit for detecting the presence or absence of at least one specific substance in a sample may comprise a first oligonucleotide sequence as described above, DNA polymerase, RNA polymerase, nucleotide triphosphates, and a means for determining the presence of RNA transcripts synthesized from the nucleotide sequence capable of transcribing RNA.

The present invention may be further understood by reference to the following illustrative examples.

EXAMPLES

Example 1

Geometric signal amplification occurs via two stages. In the first phase, Probe A, a portion of which is complementary to the target, hybridizes to the target. Attached to Probe A is a single stranded (inactive) RNA polymerase binding site. Next, another single stranded DNA, Probe B, hybridizes to the already captured Probe A. The second hybridization converts the inactive RNA polymerase binding site to a double stranded (active) form (FIG. 1). An RNA polymerase, such as T7 or SP6, that requires double stranded RNA polymerase binding site for binding, transcribes from the active double stranded RNA polymerase binding site in a linear reaction. This is expected to generate between 10 and 1,000 times more RNA than there was original target. The actual quantity depends on how much original target there is and the concentrations of the nucleotide triphosphates added to the mixture, as well as the reaction time.

In the second phase of the process, the new RNA transcripts hybridize to additional Probe A, already present in the reaction mixture. The newly created transcripts are then utilized as primers for DNA synthesis to recreate the double stranded RNA polymerase binding site. The new binding site can then start the whole cycle over again. Thus, the reaction becomes geometric.

The advantage of this approach is that it produces a geometric increase in the signal. This approach does not directly amplify the target, and therefore, is good for diagnostic purposes.

A suitable procedure for carrying out this technique, therefore, involves the following process steps:

1) Immobilize target to a solid phase, via capture or membrane binding.
2) Hybridize Probe A to target. Wash away excess probe.
3) Hybridize Probe B to Probe A, thereby creating a double stranded RNA polymerase binding site. Wash away excess probe.
4) Add additional Probe A, double strand specific RNA polymerase, DNA dependent DNA Polymerase capable of using RNA primers (such as T7 DNA polymerase or E. Coli Pol 1), NTP's, dNTP's, reaction buffer for polymerases, and biotinylated NTP as label (other label alternatives are possible).
5) Transcribe from the double stranded RNA polymerase binding site created by the hybridization of Probe A to Probe B.
6) Hybridize transcripts to excess Probe A.
7) Synthesize new DNA using RNA primer to create new double stranded DNA containing a new double stranded RNA polymerase binding site.
8) The geometric cycle is formed by steps 4–6.

Example 2

Example 2 is a variation of Example 1. The variation occurs in a secondary amplification reaction. The first phase reaction creates the double stranded RNA polymerase binding site and is transcribed as in Example 1. Inside the RNA transcript are the start and end sequences of a single strand RNA virus, such as Q Beta. Thus, the first transcription reaction creates an internal RNA virus fragment which can then be replicated by an RNA dependent RNA polymerase (a replicase). There are a number of different RNA virus replicases that could be utilized for this type of reaction. There is a primary transcription reaction followed by a secondary amplification from these new transcripts. There is no cycling back to start the reaction over again.

The advantage of this method, similar to Example 1, is a large signal amplification. There are only two hybridization steps, followed by the rest of the transcription and replication steps being automatic. Such an amplification scheme may yield a billion fold amplification in only 20 minutes or so.

An illustrative procedure for carrying out this technique involves the following process steps:

1) Immobilize target to a solid phase, via capture or membrane binding.
2) Hybridize Probe A to target, wash away excess probe.
3) Hybridize Probe B (primary amplifier) to Probe A, thereby creating a double stranded double strand specific RNA polymerase binding site, wash away excess probe.
4) Add double strand specific RNA polymerase, Q Beta Replicase, NTP's, Reaction buffer for polymerases, and biotinylated NTP as label (other label alternatives are possible).
5) Transcribe from the double stranded RNA polymerase binding site created by the hybridization of Probe A to Probe B.
6) Replicate the internal portion of the newly transcribed RNA virion.
7) The geometric cycle is from steps 4 and 5.

Example 3

The advantage of this method is in its resistance to background amplification from non-specific binding. The RNA polymerase binding site cannot be created without having the probe bound to target. This also permits the addition of all reagents in a single step. Some compromises may be necessary for all reaction conditions, but the polymerases have relatively similar reaction conditions.

This method has some limitations in the nature of the target molecules that are utilizable. The targets must have a 3'OH that can be used as a primer for the DNA synthesis reaction. This makes the reaction ideal for linear viruses like HIV and HPV, or for linearized molecules through restriction enzyme cutting or DNA shearing.

The procedure for carrying out this technique is as follows:

1) Add Probe A, DNA dependent DNA polymerase, such as T7 or E. coli Pol 1, double strand binding site specific RNA polymerase, dNTP's, NTP's, and reaction buffer, and labeled NTP.
2) Hybridize Probe A to target with a 3' end, such that the 3'OH binds to the probe region and is not dangling. No removal of the original probe is necessary and this probe is utilized subsequently in step 5.
3) Using the 3'OH and DNA dependent DNA polymerase, synthesize the remaining portion of the complementary strand of Probe A. This will create a double stranded RNA polymerase binding site. Transcribe using RNA polymerase.
4) The transcripts hybridize to excess Probe A remaining after step 2.
5) Using this newly transcribed RNA as a primer, synthesize new double stranded DNA and thereby recreate the double stranded RNA polymerase binding site.
6) The geometric cycle is formed by steps 3–5.

Example 4

Background is a constant problem in amplification as well as DNA probe based detection assays. There are other signal amplifying reactions, which have been described, such as those developed by ImClone and Chiron; but these do not address non-specific binding. Chiron's methodology is excessively complicated and difficult to control. These other methods do not address the lack of specificity due to non-specific binding, which results in high background. Any non-specifically bound probe can be built into a large signal. From the practical standpoint, it appears that these approaches work moderately well, but have limited amplification and may give false positives due to non-specific background. The present inventive process is inherently less prone to false signals due to non-specific binding and, in addition, can be modified to include novel methods of background removal and two of these are shown below.

The approach of the present invention is to limit or prevent non-specific binding from being able to be amplified. The method illustrated in Example 3 is the most resistant to false signals because the amplification has a near absolute dependence on the probe's binding to the target. The DNA synthesis step cannot take place unless the probe is bound to the target and there must be a 3'OH available.

The specificity of the technique of Example 1 is in the formation of the RNA polymerase binding site. Since double stranded DNA is required for transcription, Probe A does not permit transcription by itself. In the procedure, Probe A is hybridized to the target and excess is washed away. Then Probe B is hybridized to the Probe A/target complex to allow transcription to begin. Thus, no transcription can occur unless Probe B binds to Probe A.

Figure 3:
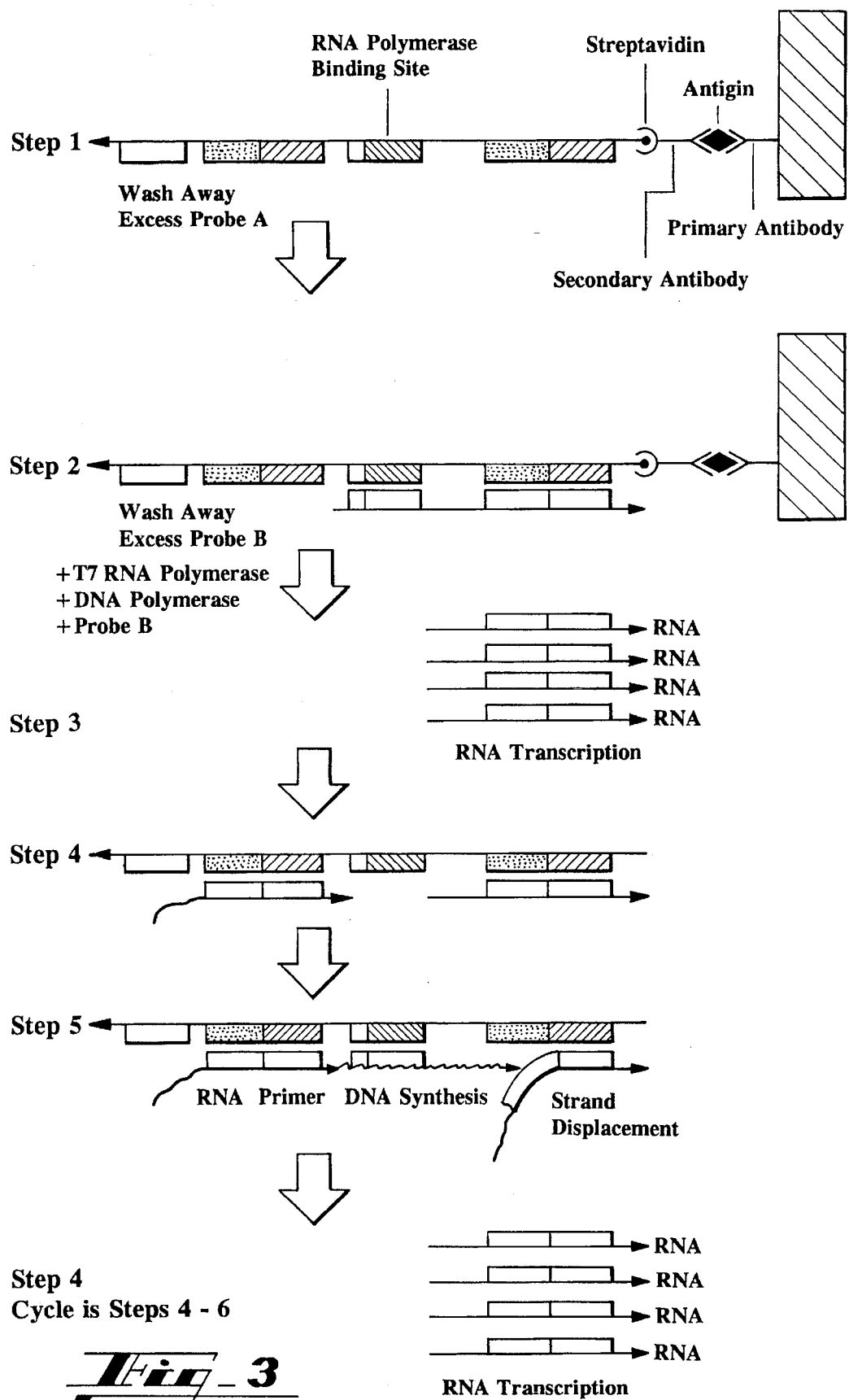
FIG. 3 depicts a preferred process of the present invention for detecting antibodies in a sample using two oligonucleotides and DNA synthesis.

It is possible for Probe A to bind non-specifically to the solid phase and therefore, Probe B potentially could bind to this non-specifically bound Probe A and transcription could take place. However, transcription should be limited because of the mechanism of non-specific binding of Probe A to the solid phase. If the non-specific binding occurs only at the 3' end of the probe, then hybridization of Probe B would not be impeded, and transcription would occur. However, if non-specific binding occurs at multiple points along Probe A as expected, then hybridization of Probe B would result in regions of single stranded DNA in the hybrid at the sites where Probe A is bound to the solid phase. These single stranded regions would terminate transcription prematurely or prevent transcription altogether. Reduction of the length of the RNA Primer Binding Region (shown in FIGS. 1 and 3) to a small portion of the 5' end limits the capability of the run-off RNA transcripts to hybridize to the RNA Primer Binding Region and initiate DNA synthesis. By making the RNA Primer Binding Region small, only long transcripts will be able to hybridize. The result is termination of the cycling reaction due to failure of the DNA synthesis to occur.

An alternative method for background reduction involves using 3'–5' exonuclease. Some exonucleases are single strand specific. They act by cleaving nucleotides from the 3' end, and, thus, are called 3'–5' exonucleases. The probe in Examples 1–3 can be used with the RNA polymerase binding site at the 3' end of Probe A to take advantage of single strand specific 3'–5' exonuclease activity, such as Exonuclease 1 of *E. coli*. After hybridization of Probe A to the target and washing away the excess probe, the 3'–5' exonuclease is added to the reaction mixture. If the probe is bound to the target, then the RNA polymerase binding site will be double stranded and protected from the action of 3'–5' exonuclease. Wherever the probe non-specifically binds to a membrane or capture probe, the RNA polymerase binding (RPB) site will be single stranded and accessible to the exonuclease. Furthermore, the RNA polymerase binding site will be near the 3' end of the probe so that only limited exonuclease activity will be required to destroy the RPB site.

Example 5

The present inventive problems can also be utilized to increase the detection of antibody reactions. The method applies to standard ELISA type reactions in which antigen to which serum antibody binds is coated on a microtiter plate. It also works equally well with antigen capture assays in which a primary antibody to which antigen binds is coated on a microtiter plate (see FIG. 3).

The key is a connecting molecule, which links the serum antibody or antigen to the DNA probe amplifying system. The "connector molecule" may be any suitable substance which will enable the oligonucleotide probe of the present invention to bind to the specific antibody to be detailed. Preferably, this molecule is another antibody that is complexed to streptavidin. Streptavidin is the linker through which a biotinylated Probe A binds. The remainder of the amplification system is essentially the same as described in Example 1.

Example 6

This is an example of how the Signal Amplification scheme might be used in an actual diagnostic test format. The example is shown for the technique set out in Example 1. It is assumed that the target is in very small quantity; otherwise the signal amplification technology would not be used. The steps below indicate the basic application of signal amplification to a test format in a microtiter plate with a nylon or nitrocellulose filter forming the bottom of the well. In this format, the FITC becomes incorporated into newly synthesized RNA. Residual unincorporated nucleotide is removed to permit reading fluorescence without interference by binding the RNA to a filter and washing away the excess unincorporated NTP. The numbers in parentheses are estimates of the time allowed per step. The total time for sample processing is estimated at 1.5 hours to 4.25 hours.

1) Lyse cells in Lysis Solution containing guanidinium thiocyanate and SDS; filter to bind DNA/RNA. (5')
2) Add Probe A (Primary Amplifier) and hybridize. (15'–60')
3) Wash away excess Probe A. (5'–15')
4) Add Probe B and Hybridize. (15'–60')
5) Wash away excess Probe B. (5'–15')
6) Add RNA Polymerase, DNA Polymerase, Probe A, FITC-labeled NTP, Transcribe, rehybridize, synthesize, repeat cycle. (30'–60')
7) Transfer solution to a new well and filter reaction through membrane to bind newly synthesized RNA. (5'–15')
8) Wash away excess unincorporated FITC-NTP. (5'–15')
9) Read residual fluorescence in well. (10')

Example 7

The following scheme is shown for the technique set out in Example 3. Only steps 6–9 are different from Example 6 above. In this format, the RNA is double labeled with both biotin for binding to the streptavidin coated plates and with FITC for reading the fluorescence. The excess FITC is removed by washing the plate after capture to permit reading only the incorporated fluorescence. A limited quantity of biotinylated NTP may be used to avoid competing with the biotin labeled RNA. The total time is 1.75 hours to 5 hours.

6) Add RNA Polymerase, DNA Polymerase, Probe A, FITC-labeled NTP, Biotinylated NTP, Transcribe, rehybridize, synthesize, repeat cycle. (30'–60')

7) Transfer solution to a new well coated with streptavidin and capture the biotinylated RNA that is also labeled with FITC. (15'60')

8) Wash away excess FITC-NTP. (5'–15')

9) Read fluorescence. (10')

Example 8

As illustrated in FIG. 4, background may be reduced using restriction enzyme digestion. A suitable procedure for carrying out this technique involves the following process steps:

1) Immobilize target to a solid phase.

2) Hybridize Probe A to target. Wash away excess Probe A.

3) Add restriction enzyme and reaction buffer.

4) Incubate in order to cut DNA.

5) Filter to collect specifically bound probe.

6) Continue with amplification, following the steps shown in Examples 1, 2, or 3.

Example 9

As shown in FIG. 5, background may also be reduced by denaturation of the specifically bound probe. A suitable procedure for carrying out this technique involves the following process steps:

1) Immobilize target to a solid phase.

2) Hybridize Probe A to target. Wash away excess Probe A.

3) Denature, e.g., by heating the solution or by adding alkali.

4) Separate soluble material from the solid phase, e.g., by filtration or centrifugation.

5) Continue with amplification, following the steps shown in Examples 1 or 2.

Example 10

Target nucleic acid sequences may also be detected using a probe as shown in FIG. 6. The process steps follow are described in Examples 1, 2, or 3.

While this invention has been described with an emphasis upon preferred embodiments, it will be obvious to those of ordinary skill in the art that variations in the preferred processes and kits may be used and that it is intended that the invention may be practiced otherwise than as specifically described herein. Accordingly, this invention includes all modifications encompassed within the spirit and scope of the following claims.

What is claimed is:

1. A process for detecting the presence or absence of at least one specific nucleic acid in a sample containing a nucleic acid or mixture of nucleic acids, which process comprises:

(a) immobilizing said specific nucleic acid to be detected, (b) treating the sample with a first oligonucleotide under hybridizing conditions such that a portion of said first oligonucleotide hybridizes to the 3' end of said specific nucleic acid to be detected and a portion of said first oligonucleotide does not hybridize to said specific nucleic acid to be detected, wherein said portion of said first oligonucleotide which does not hybridize to said specific nucleic acid to be detected forms a double-stranded RNA polymerase binding site and a nucleotide sequence transcribing RNA when hybridized to a complementary nucleotide sequence in the absence of nucleic acid extension, (c) treating the sample to remove any of the first oligonucleotide which is not hybridized to said specific nucleic acid to be detected, (d) treating the sample with a second oligonucleotide under hybridizing conditions such that said second oligonucleotide hybridizes to said portion of said first oligonucleotide which does not hybridize to said specific nucleic acid to be detected and forms a double-stranded RNA polymerase binding site and nucleotide sequence transcribing RNA, (e) treating the sample with RNA polymerase and nucleotide triphosphates such that said nucleotide sequence formed between a portion of said first oligonucleotide and a portion of said second oligonucleotide results in the synthesis of RNA transcripts from the nucleotide sequence transcribing RNA wherein the sequence of the nucleic acid to be detected is not transcribed, and (f) determining whether said RNA transcripts were synthesized.

2. The process of claim 1, wherein the sample at step (e) is further treated with said first oligonucleotide and with DNA polymerase such that said first oligonucleotide hybridizes to said RNA transcripts which act as primers for synthesis of an extension nucleotide sequence complementary to said first oligonucleotide to form a double-stranded RNA polymerase binding site and a nucleotide sequence transcribing RNA which results in the synthesis of additional RNA transcripts.

3. The process of claim 2, wherein the step of treating the sample with said first oligonucleotide sequence and with DNA polymerase is repeated.

4. The process of claim 1, wherein said RNA transcripts are virus fragments and are replicated through use of an RNA virus replicase.

5. The process of claim 1, wherein the sample at step (c) is further treated to separate said first oligonucleotide sequence from said specific nucleic acid sequence to be detected.

6. The process of claim 5, wherein said first oligonucleotide sequence is separated from said specific nucleic acid sequence to be detected by denaturation.

7. The process of claim 1, wherein the sample at step (d) is further treated to separate said first oligonucleotide from said specific nucleic acid to be detected resulting in a soluble portion of said first oligonucleotide hybridized to said second oligonucleotide sequence forming a double-stranded RNA polymerase binding site and a nucleotide sequence transcribing RNA.

8. The process of claim 7, wherein said first oligonucleotide sequence is separated from said specific nucleic acid sequence to be detected through use of a restriction enzyme which cleaves the portion of said first oligonucleotide sequence hybridized to said specific nucleic acid sequence to be detected.

9. The process of claim 1, wherein said portion of said first oligonucleotide sequence which hybridizes to said second oligonucleotide sequence includes a nucleotide sequence non-identical and a nucleotide sequence identical to said portion of said first oligonucleotide sequence which hybridizes to said specific nucleic acid sequence to be detected.

10. The process of claim 9, wherein said portion of said first oligonucleotide sequence which hybridizes to said second oligonucleotide sequence is identical to said portion of said first oligonucleotide sequence which hybridizes to said specific nucleic acid sequence to be detected.

11. A process for detecting the presence or absence of at least one specific nucleic acid in a sample containing a nucleic acid or mixture of nucleic acids, which process comprises:

(a) immobilizing said specific nucleic acid to be detected, (b) treating the sample with an oligonucleotide under hybridizing conditions such that a portion of said oligonucleotide hybridizes to the 3' end of said specific nucleic acid to be detected which acts as a primer for said oligonucleotide and a portion of said oligonucleotide does not hybridize to said specific nucleic acid to be detected, wherein said portion of said oligonucleotide which does not hybridize to said specific nucleic acid to be detected forms an RNA polymerase binding site and a nucleotide sequence transcribing RNA when an extension product is synthesized from said primer, wherein said extension product is complementary to said portion of the oligonucleotide that does not hybridize to the specific nucleic acid to be detected, (c) treating the sample with DNA polymerase, RNA polymerase, and nucleotide triphosphates such that an extension product is synthesized from said primer which is complementary to said oligonucleotide to form a double-stranded RNA polymerase binding site and a nucleotide sequence transcribing RNA which results in the synthesis of RNA transcripts from the nucleotide sequence transcribing RNA, wherein the sequence of the nucleic acid to be detected is not transcribed, and (d) treating the RNA transcripts with said oligonucleotide and DNA polymerase such that the oligonucleotide hybridizes to the RNA transcripts, which act as primers for synthesis of an extension nucleotide sequence complementary to the oligonucleotide, to form a double-stranded RNA polymerase binding site and a nucleotide sequence transcribing RNA, resulting in the synthesis of additional RNA transcripts from the nucleotide sequence transcribing RNA, wherein the sequence of the nucleic acid to be detected is not transcribed, and (e) determining whether said RNA transcripts were synthesized.

12. The process of claim 11 wherein the step of treating the sample with said oligonucleotide sequence and with DNA polymerase is repeated.

13. The process of claim 11 wherein said RNA transcripts are virus fragments and are replicated through use of an RNA virus replicase.

* * * * *